United States Patent [19]

Scoggins et al.

[11] B 4,000,159
[45] Dec. 28, 1976

[54] PREPARATION OF N,N-DISUBSTITUTED THIOAMIDES
[75] Inventors: Lacey E. Scoggins; Donald H. Kubicek, both of Bartlesville, Okla.
[73] Assignee: Phillips Petroleum Company, Bartlesville, Okla.
[22] Filed: June 28, 1974
[21] Appl. No.: 484,269
[44] Published under the second Trial Voluntary Protest Program on February 10, 1976 as document No. B 484,269.
[52] U.S. Cl. .................. 260/326.5 FN; 260/551 S
[51] Int. Cl.$^2$ ............ C07C 153/057; C07D 207/26
[58] Field of Search ... 260/326.45, 551 S, 326.5 FN
[56] References Cited
UNITED STATES PATENTS

| 2,368,515 | 1/1945 | Blake | 260/551 S UX |
|---|---|---|---|
| 2,531,283 | 11/1950 | Levesque | 260/551 S |
| 2,539,325 | 1/1951 | Prochazka | 260/239.3 R |
| 2,560,296 | 7/1951 | Levesque | 260/551 S |
| 3,192,210 | 6/1965 | Lansford et al. | 260/326.45 X |

OTHER PUBLICATIONS

Hurd et al., Chem. Rev. 61, 45, (1961), pp. 46–49.

*Primary Examiner*—Allen B. Curtis

[57] ABSTRACT

N,N-disubstituted thioamides are prepared by contacting N,N-disubstituted amides with carbon disulfide or carbon oxysulfide under suitable reaction conditions. In a preferred embodiment, the reactants are contacted at a temperature of at least about 200° C and a pressure sufficient to maintain the reactants in the liquid phase at the reaction temperature.

8 Claims, No Drawings

PREPARATION OF N,N-DISUBSTITUTED THIOAMIDES

BACKGROUND OF THE INVENTION

This invention relates to the preparation of sulfur-containing compounds. In one aspect, this invention relates to the preparation of N,N-disubstituted thioamides. In another of its aspects, this invention relates to the reaction of N,N-disubstituted amides with a sulfide compound.

It is known that lactams can be reacted with elemental sulfur or hydrogen sulfide to produce thiolactams. It is also known that certain lactams such as 4-butyrolactam and 6-caprolactam can be reacted with carbon disulfide to produce the corresponding thiolactam as shown in the process of U.S. Pat. No. 2,539,325. The processes set out in that patent, however, are not effective in the production of all N-monosubstituted thioamides from the corresponding N-monosubstituted amide. We have found, for instance, that 2-pyrrolidone when contacted with carbon disulfide under elevated temperature and pressure results in the production of little or none of the corresponding N-monosubstituted thioamide.

In contrast of this, we have found that contacting N,N-disubstituted amides under suitable reaction conditions with a sulfide selected from carbon disulfide and carbon oxysulfide results in the production of the corresponding N,N-disubstituted thioamide, so that, while an N-monosubstituted amide such as 2-pyrrolidone, which is outside the scope of this invention, does not react to produce the corresponding N-monosubstituted thioamide, an N,N-disubstituted amide such as N-methyl-2-pyrrolidone can be reacted under otherwise similar conditions to produce the corresponding N,N-disubstituted thioamide.

Therefore, in accordance with this invention, N,N-disubstituted thioamides are produced by contacting under suitable reaction conditions an N,N-disubstituted amide with a sulfide selected from carbon disulfide and carbon oxysulfide.

The amides employed in the process of this invention can be represented by the formula

wherein each R is a hydrocarbyl radical selected from alkyl, cycloalkyl, aryl, and combinations thereof such as alkaryl, aralkyl, and the like, the number of carbon atoms in each R being within the range of 1 to about 20, R' is selected from R and hydrogen, and the total number of carbon atoms in said amide is within the range of 3 to about 30, with the proviso that R' and one R together can be - $(CR''_2)_n$ -, wherein R'' is selected from hydrogen, alkyl, cycloalkyl, and aryl, and combinations thereof such as alkaryl, aralkyl, and the like, n is an integer of 2 to about 12, and the total number of carbon atoms in - $(CR''_2)_n$ - is within the range of 2 to about 20.

Example of some amides which can be employed in the process of this invention include N,N-dimethylformamide, N,N-dimethylacetamide, N-ethyl-N-isopropylpropionamide, N,N-dibutylhexanamide, N-isobutyl-N-octyldecanamide, N,N-dicyclohexylhexadecanamide, N-propyl-N-hexylheneicosanamide, N,N-didodecyl-3-methylpentanamide, N-methyl-N-eicosylcyclohexanecarboxamide, N,N-diphenyl-p-toluamide, N-methyl-N-benzylbenzamide, N-ethyl-N-m-tolyl-3-phenylbutyramide, N-methyl-2-azetidinone, N-methyl-2-pyrrolidone, N-ethyl-2-piperidone, N-isopropyl-2-oxohexamethylenimine, lactam of 7-(butylamino)heptanoic acid, lactam of 10-(benzylamino)decanoic acid, lactam of 13-(hexylamino)-tridecanoic acid, N-cyclopentyl-3-methyl-2-azetidinone, N-o-tolyl-3-ethyl-4-isopropyl-2-pyrrolidone, N-phenyl-3-hexyl-5-p-tolyl-2-piperidone, N-propyl-2-oxo3-cyclohexyl-5-phenylhexamethylenimine, N-isobutyl-4-benzyl-2-piperidone, N-decyl-3-dodecyl-2-pyrrolidone, N-nonyl-4-octadecyl-2-azetidinone, and the like, and mixtures thereof.

The thioamides produced in the process of this invention can be represented by the formula

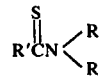

wherein each R is a hydrocarbyl radical selected from alkyl, cycloalkyl, aryl, and combinations thereof such as alkaryl, aralkyl, and the like, the number of carbon atoms in each R being within the range of 1 to about 20, R' is selected from R and hydrogen, and the total number of carbon atoms in said thioamide is within the range of 3 to about 30, with the proviso that R' and one R together can be - $(CR''_2)_n$ -, wherein R'' is selected from hydrogen, alkyl, cycloalkyl, and aryl, and combinations thereof such as alkaryl, aralkyl, and the like, n is an integer of 2 to about 12, and the total number of carbon atoms in - $(CR''_2)_n$ - is within the range of 2 to about 20.

Examples of some thioamides which can be produced by the process of this invention include N,N-dimethylthioformamide, N,N-dimethylthioacetamide, N-ethyl-N-isopropylthiopropionamide, N,N-dibutylthiohexanamide, N-isobutyl-N-octylthiodecanamide, N,N-dicyclohexylthiohexadecanamide, N-propyl-N-hexylthioheneicosanamide, N,N-didodecyl-3-methylthiopentanamide, N-methyl-N-eicosylthiocyclohexanecarboxamide, N,N-diphenylthio-p-toluamide, N-methyl-N-benzylthiobenzamide, N-ethyl-N-m-tolyl-3-phenylthiobutyramide, N-methyl-2-azetidinethione, N-methyl-2-pyrrolidinethione, N-ethyl-2-piperidinethione, N-isopropyl-2-thioxohexamethylenimine, thiolactam of 7-(butylamino)dithioheptanoic acid, thiolactam of 10-(benzylamino)dithiodecanoic acid, thiolactam of 13-(hexylamino)dithiotridecanoic acid, N-cyclopentyl-3-methyl-2-azetidinethione, N-o-tolyl-3-ethyl-4-isopropyl-2-pyrrolidinethione, N-phenyl-3-hexyl-5-p-tolyl 2-piperidinethione, N-propyl-2-thioxo-3-cyclohexyl-5-phenylhexamethylenimine, N-isobutyl-4-benzyl-2-piperidinethione, N-decyl-3-dodecyl-2-pyrrolidinethione, N-nonyl-4-octadecyl-2-azetidinethione, and the like, and mixtures thereof.

The ratio of carbon disulfide or carbon oxysulfide to N,N-disubstituted amide employed in the process of this invention should be such as to provide about 0.2 to about 20, preferably about 0.3 to about 12, gram-atoms of sulfur in the carbon disulfide or carbon oxysulfide per gram-mole of amide. The reaction temperature can vary over a considerable range, but should be maintained at a level below that at which substantial thermal decomposition of the reactants or products can occur. The reaction temperature generally will be within the range of about 200°C to about 350°C, preferably about 220°C to about 300°C. The reaction time can vary over a wide range, depending in part on the reaction temperature, but will be within the general range of about 1 minute to about 2 days, preferably about 30 minutes to about 10 hours. The reaction pressure will be within the general range of about 0 psig to about 5000 psig, preferably about 100 psig to about 2000 psig. The reactants, preferably, are contacted at a pressure and reaction temperature at which the reactants are maintained substantially in the liquid phase. Diluents or solvents inert to the reactants and products under the conditions of reaction can be used if desired. Diluents or solvents which can be present include saturated aliphatic, saturated cycloaliphatic, and aromatic hydrocarbons such as hexane, heptane, 2-methyl-heptane, cyclopentane, cyclohexane, methylcyclopentane, benzene, toluene, xylenes, and the like, and mixtures thereof. The reaction can be carried out in a continuous or batch process.

Upon completion of the reaction, the thioamide can be separated from the reaction mixture by conventional processes such as distillation, crystallization, solvent extraction, or the like.

The thioamides of this invention are useful in various applications, e.g., as vulcanization accelerators, insecticides, fungicides, corrosion inhibitors, lubricating oil additives, and in the production of arylene sulfide polymers.

EXAMPLE I

To a 1-liter stirred autoclave were added 300 ml (5.0 gram-moles) of carbon disulfide and 100 ml (1.1 gram-moles) of N,N-dimethylacetamide. The reactor was sealed and the mixture was heated to 250°C with stirring. After 3 hours at this temperature, the mixture exhibited a pressure of about 800 psig. Although the pressure was still rising slowly, the reaction was terminated at this point by cooling. Gas chromatographic analysis of a sample of the reaction mixture indicated it contained approximately equal weights of unreacted N,N-dimethylacetamide and a compound subsequently identified as the desired N,N-dimethylthioacetamide. From the reaction mixture was obtained by distillation 57.3 g (52 percent batch yield or an ultimate yield of about 95 percent, each based on N,N-dimethylacetamide) of N,N-dimethylthioacetamide which solidified to a slightly yellow solid. A small portion of this solid was crystallized from methanol to give the purified N,N-dimethylthioacetamide as a nearly white solid which was subjected to elemental analysis. Analysis (weight percent). Calculated for N,N-dimethylthioacetamide: C, 46.66; H, 8.79; N, 13.58; S, 31.08 Found: C, 46.66; H, 8.75; N, 13.38; S, 31.0.

EXAMPLE II

To a 2-liter stirred reactor were added 1030 g (10.4 gram-moles) of N-methyl-2-pyrrolidone and 152 g (2 gram-moles) of carbon disulfide. The reactor was sealed and heated to 253°C, at which temperature the pressure was 260 psig. After 2 ⅓ hours at about 255°C the pressure had increased to 410 psig, at which time the reactor was cooled. The mixture was degassed by venting the reactor at a temperature of 190°C with slow stirring. A dark liquid, 1083 g, was drained from the reactor. Gas chromatographic analysis of this liquid indicated the presence of two major components having retention times corresponding to those of N-methyl-2-pyrrolidone and N-methyl-2-pyrrolidinethione. Based on the ratio of N-methyl-2-pyrrolidinethione to N-methyl-2-pyrrolidone, as determined gas chromatographically, and the carbon disulfide charged to the reactor, the batch yield of N-methyl-2-pyrrolidinethione was 69 percent.

EXAMPLE III

To a 2-liter stirred reactor were charged 1000 g (10.1 gram-moles) of N-methyl-2-pyrrolidone and 200 g (2.63 gram-moles) of carbon disulfide. The reactor was sealed and pressured to 20 psig with nitrogen. The mixture was heated to 254°C, resulting in a pressure of 285 psig. After 110 minutes the reactor pressure had increased to 420 psig, and a second charge of 108.4 g (1.43 moles) of carbon disulfide was pumped into the reactor, bringing the pressure to 480 psig. Within 62 minutes the pressure had increased to 560 psig. A third and final charge of 104 g (1.37 moles) of carbon disulfide was then pumped into the reactor, boosting the pressure to 570 psig. After 295 minutes total reaction time at a temperature of 252°–254°C the reactor at 600 psig was cooled to 26°C. The gas phase (100 psig) was vented, and a sample of the vented gas was found to contain 70 weight percent carbon dioxide, 15 weight percent carbon oxysulfide, 10 weight percent carbon disulfide, and 5 weight percent hydrogen sulfide. From the reactor liquid effluent were distilled 109.2 g of carbon disulfide, 549.7 g of N-methyl-2-pyrrolidone boiling at 92°–93°C/13 mm Hg, and 465 g (40 percent batch yield or 89 percent ultimate yield, each based on N-methyl-2-pyrrolidone) of N-methyl-2-pyrrolidinethione boiling at 132°–135°C/13 mm Hg, $n_D^{20}$ 1.5825, which was subjected to elemental analysis. Analysis (weight percent). Calculated for N-methyl-2-pyrrolidinethione: C, 52.14; H, 7.87; N, 12.16; S, 27.83. Found: C, 52.39; H, 7.93; N, 12.06; S, 27.8.

EXAMPLE IV

By a process outside the scope of this invention an attempt was made to prepare 2-pyrrolidinethione. To a 1-liter stirred autoclave were added 100 g (1.2 gram-moles) of 2-pyrrolidone and 500 g (6.6 gram-moles) of carbon disulfide. The mixture was heated with stirring at 200°C for 2 hours, resulting in a pressure of 400 psig. Gas chromatographic analysis of the dark reaction mixture gave evidence of nothing other than carbon disulfide and 2-pyrrolidone. Distillation of the unreacted carbon disulfide and most of the unreacted 2-pyrrolidone gave 11.5 g of pot residue which contained chiefly 2-pyrrolidone and a small amount of another substance which could possibly have been 2-pyrrolidinethione. In any event, this was not a satisfactory procedure for the preparation of 2-pyrrolidinethione.

EXAMPLE V

Another attempt was made to prepare 2-pyrrolidinethione by a process outside the scope of this invention. The run was conducted as in Example IV except that it was carried out at 240°C for 4 hours instead of at 200°C for 2 hours. Gas chromatographic analysis of the resulting reaction mixture gave evidence of nothing other than carbon disulfide and 2-pyrrolidone. Distillation of the unreacted carbon disulfide and 45 g of unreacted 2-pyrrolidone gave 55 g of black pot residue. Gas chromatographic analysis of this pot residue indicated the presence of no component which appeared to be 2-pyrrolidinethione. Attempts to obtain crystalline 2-pyrrolidinethione from the pot residue by extraction and crystallization with xylene yielded only intractable solids. Thus, this was not a satisfactory procedure for the preparation of 2-pyrrolidinethione.

We claim:

1. A method for preparing N,N-disubstituted thioamides consisting essentially of contacting at an elevated temperature in a range of 200°C to 350°C a sulfide selected from carbon disulfide or carbon oxysulfide with an N,N-disubstituted amide represented by the formula

wherein each R is a hydrocarbyl radical selected from alkyl, cycloalkyl, aryl, and combinations thereof such as alkaryl, aralkyl, and the like, the number of carbon atoms in each R being within the range 1 to about 20, R' is selected from R and hydrogen, and the total number of carbon atoms in each of said amide or thioamide is within the range of 3 to about 30, with the proviso that R' and one R together can be - $(CR''_2)_n$ -, wherein R'' is selected from hydrogen, alkyl, cycloalkyl, and aryl, and combinations thereof such as alkaryl, aralkyl, and the like, n is an integer of 2 to about 12, and the total number of carbon atoms in - $(CR''_2)_n$ - is within the range of 2 to about 20, to produce a thioamide product represented by the formula

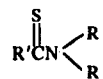

wherein R, R', and R'' are the same as described above.

2. A method of claim 1 wherein the ratio of sulfide reactant to N,N-disubstituted amide reactant provides from about 0.2 to about 20 g atoms of sulfur in the sulfide reactant per gram mole of amide reactant.

3. A method of claim 1 wherein the reaction temperature is in a range of about 220°C to about 300°C.

4. A method of claim 3 wherein the reaction pressure is in a range of about 100 to about 2,000 psig.

5. A method of claim 1 wherein the reaction pressure is in a range of about 0 to about 5,000 psig.

6. A method of claim 4 wherein the N,N -disubstituted amide is N,N-dimethylacetamide and the sulfide is carbon disulfide.

7. The method of claim 4 wherein the N,N-disubstituted amide is N-methyl-2-pyrrolidone and the sulfide is carbon disulfide.

8. A method of claim 1 wherein the reactants are contacted in the presence of diluents or solvents inert to the reactants and products at the conditions of reaction.

* * * * *